United States Patent
Kweon et al.

(10) Patent No.: US 12,039,729 B2
(45) Date of Patent: Jul. 16, 2024

(54) METHOD AND DEVICE FOR AUTOMATICALLY PROCESSING BLOOD VESSEL IMAGE

(71) Applicant: MEDIPIXEL, INC., Seoul (KR)

(72) Inventors: Jihoon Kweon, Gyeonggi-do (KR); Young-Hak Kim, Seoul (KR); Hwi Kwon, Seoul (KR)

(73) Assignee: MEDIPIXEL, INC., Seoul (KR)

( * ) Notice: Subject to any disclaimer, the term of this patent is extended or adjusted under 35 U.S.C. 154(b) by 0 days.

(21) Appl. No.: 17/924,678

(22) PCT Filed: Feb. 5, 2021

(86) PCT No.: PCT/KR2021/001538
§ 371 (c)(1),
(2) Date: Nov. 10, 2022

(87) PCT Pub. No.: WO2021/246612
PCT Pub. Date: Dec. 9, 2021

(65) Prior Publication Data
US 2023/0196559 A1    Jun. 22, 2023

(30) Foreign Application Priority Data
Jun. 2, 2020 (KR) .................. 10-2020-0066267

(51) Int. Cl.
*G06T 7/00* (2017.01)
*G06T 5/77* (2024.01)
(Continued)

(52) U.S. Cl.
CPC .............. *G06T 7/0012* (2013.01); *G06T 5/77* (2024.01); *G06T 7/11* (2017.01); *G06T 7/60* (2013.01);
(Continued)

(58) Field of Classification Search
CPC ......... G06T 7/0012; G06T 5/005; G06T 7/11; G06T 7/60; G06T 2207/30101;
(Continued)

(56) References Cited

U.S. PATENT DOCUMENTS 10,470,730 B2    11/2019  Benishti et al.
10,524,755 B2     1/2020  Kowarschik et al.
(Continued)

FOREIGN PATENT DOCUMENTS

CN    101551862 A    10/2009
CN    102404595 B    11/2013
(Continued)

OTHER PUBLICATIONS

Chapman et al. "Automated Generation of Directed Graphs from Vascular Segmentations." Journal of Biomedical Informatics, 56, 2015, pp. 395-405 (Year: 2015).*

(Continued)

*Primary Examiner* — Jon Chang
(74) *Attorney, Agent, or Firm* — MARSHALL, GERSTEIN & BORUN LLP

(57) ABSTRACT

A method, performed by a processor, for processing a blood vessel image from an angiography image may comprise the steps of: extracting a target blood vessel from a blood vessel image; identifying an error portion from the extraction result of the target blood vessel on the basis of at least one of blood vessel structure data related to the target blood vessel, curvature information of the target blood vessel, diameter information of the target blood vessel, and brightness information of the target blood vessel; and in response to a case where an error portion is identified in the target blood vessel, correcting the identified error portion.

10 Claims, 12 Drawing Sheets

(51) Int. Cl.
*G06T 7/11* (2017.01)
*G06T 7/60* (2017.01)
*G06V 10/44* (2022.01)
*G06V 10/98* (2022.01)

(52) U.S. Cl.
CPC .......... *G06V 10/457* (2022.01); *G06V 10/993* (2022.01); *G06T 2207/30101* (2013.01); *G06T 2207/30168* (2013.01); *G06V 2201/03* (2022.01)

(58) Field of Classification Search
CPC ............. G06T 2207/30168; G06T 5/77; G06T 2207/20081; G06T 2207/20084; G06T 2207/20096; G06T 7/187; G06T 2200/24; G06T 2207/10116; G06V 10/457; G06V 10/993; G06V 2201/03; A61B 6/467; A61B 6/469; A61B 6/504; A61B 6/481; A61B 6/5217; A61B 6/5258; G16H 30/40
See application file for complete search history.

(56) References Cited

U.S. PATENT DOCUMENTS

| | | | | |
|---|---|---|---|---|
| 2014/0355858 | A1* | 12/2014 | O'Dell | G06T 7/11 382/131 |
| 2016/0022236 | A1* | 1/2016 | Ohishi | G16H 50/30 600/431 |
| 2016/0328855 | A1 | 11/2016 | Lay et al. | |
| 2022/0047236 | A1* | 2/2022 | Lavi | A61B 6/504 |

FOREIGN PATENT DOCUMENTS

| | | |
|---|---|---|
| CN | 108205807 A | 6/2018 |
| JP | 2004-283373 A | 10/2004 |
| JP | 2011-212314 A | 10/2011 |
| JP | 2013-090799 A | 5/2013 |
| JP | 2014-180492 A | 9/2014 |
| JP | 2019521733 A | 8/2019 |
| KR | 10-2013-0028534 A | 3/2013 |
| KR | 10-2016-0043988 A | 4/2016 |
| KR | 20160053325 A | 5/2016 |
| KR | 20190084380 A | 7/2019 |
| KR | 10-2019-0100005 A | 8/2019 |
| KR | 10-2395873 | 5/2022 |

OTHER PUBLICATIONS

International Search Report for PCT/KR2021/001538, dated May 14, 2021.
First Office Action issued in KR Application No. 10-2020-0066267 dated Jan. 9, 2022, 10 pages.
Notice of Allowance issued in KR Application No. 10-2020-0066267 dated Apr. 20, 2022, 4 pages.

* cited by examiner

METHOD AND DEVICE FOR AUTOMATICALLY PROCESSING BLOOD VESSEL IMAGE

TECHNICAL FIELD

The following description relates to a method for processing a blood vessel image.

BACKGROUND ART

Angiography images are widely used to diagnose error portions within blood vessels by observing main blood vessels and perform necessary procedures and measures. Conventionally, image processing engines for automatically identifying main blood vessels from a blood vessel image have been used in order to increase convenience and quantify a diagnosis result. For example, a Caas QCA engine from Pie Medical Imaging B. V. may find and display main blood vessels in the angiography images. On the other hand, the main blood vessels extracted from the engine often show errors, such as blood vessel portions (misidentification) other than the main blood vessels to be extracted, a portion (disconnection) to be disconnected, or the like. Therefore, in clinical practices, an identification result obtained by first extracting the main blood vessels from the engine is not used as it is, but manpower is input to check the angiography image, and the errors are directly corrected by the manpower and then the corrected errors are used and stored.

The above-mentioned background art is possessed or acquired by the inventor in the process of deriving the disclosure of the present application and cannot necessarily be said to be a known technology disclosed to the general public prior to the present application.

DISCLOSURE OF THE INVENTION

Technical Goals
Technical Solutions

According to an aspect of the present disclosure, there is provided a method for processing a blood vessel image performed by a processor including the steps of: extracting a target blood vessel from a blood vessel image; identifying an error portion from the extraction result of the target blood vessel on the basis of at least one of blood vessel structure data related to the target blood vessel, curvature information of the target blood vessel, diameter information of the target blood vessel, and brightness information of the target blood vessel; and correcting the identified error portion in response to a case where the error portion is identified from the extraction result of the target blood vessel.

In an example embodiment, the identifying of the error portion of a method for processing a blood vessel image may include the steps of: segmenting a blood vessel area and a non-blood vessel area from the blood vessel image; generating the blood vessel structure data on the basis of a node corresponding to each of blood vessel branches divided based on a branch point in the blood vessel area; comparing connection data between nodes of the target blood vessel with the blood vessel structure data; and determining nodes corresponding to a connection error as the error portion when the connection error between the nodes is detected on the basis of a topology of the blood vessel structure data.

In an example embodiment, the correcting of the error portion of a method for processing a blood vessel image may include the steps of: connecting regions corresponding to a discontinuity portion in response to a case where the error portion is identified as the discontinuity portion; and replacing a node corresponding to a misidentification portion with a node matching the blood vessel structure data in response to a case where the error portion is identified as the misidentification portion.

In an example embodiment, the identifying of the error portion of a method for processing a blood vessel image may include identifying a lower branch as a misidentification portion in response to a case where a curvature between an upper branch and a lower branch adjacent to each other exceeds a threshold curvature in the extraction result of the target blood vessel.

In an example embodiment, the correcting of the error portion of a method for processing a blood vessel image may include replacing the lower branch with another candidate lower branch having a curvature with the upper branch of the threshold curvature or less with respect to the identified misidentification portion.

In an example embodiment, the identifying of the error portion of a method for processing a blood vessel image may include identifying the lower branch as an error portion in response to a case where a diameter difference between the upper branch and the lower branch adjacent to each other is a threshold or more in the extraction result of the target blood vessel.

In an example embodiment, the correcting of the error portion of a method for processing a blood vessel image may include correcting the identified error portion by performing at least one of replacing the lower branch on the basis of the diameter difference from the upper branch with respect to the identified error portion and generating a new extraction result including new diameter information about the target blood vessel.

In an example embodiment, the identifying of the error portion of a method for processing a blood vessel image may include identifying the lower branch as a misidentification portion in response to a case where a brightness difference between an upper branch and a lower branch adjacent to each other is a threshold brightness difference or more in the extraction result of the target blood vessel.

In an example embodiment, the correcting of the error portion of a method for processing a blood vessel image may include replacing the lower branch with another candidate lower branch having a brightness difference from the upper branch of less than the threshold brightness difference with respect to the identified misidentification portion.

In an example embodiment, the correcting of the error portion of a method for processing a blood vessel image may include generating a new extraction result for the target blood vessel in response to a case where the error portion is identified.

In an example embodiment, the correcting of the error portion of a method for processing a blood vessel image may include the steps of: providing a user with one or more candidate branches in response to a case where the error portion is the misidentification portion; and replacing a branch corresponding to the error portion with the selected branch in response to a case of receiving a selection input for one branch among the one or more candidate branches from the user.

In an example embodiment, the correcting of the error portion of a method for processing a blood vessel image may include connecting a region corresponding to a blood vessel branch corresponding to a start point of a user input and a region corresponding to a blood vessel branch corresponding to an end point of the user input, in response to a case where the user input is detected in a plurality of points.

According to another aspect of the present disclosure, there is provided a device for processing a blood vessel image including: an image receiver for receiving a blood vessel image; and a processor for extracting a target blood vessel from the blood vessel image, identifying an error portion from the extraction result of the target blood vessel on the basis of at least one of blood vessel structure data related to the target blood vessel, curvature information of the target blood vessel, diameter information of the target blood vessel, and brightness information of the target blood vessel, and correcting the identified error portion in response to a case where the error portion is identified from the extraction result of the target blood vessel.

Advantageous Effects

The method for processing the blood vessel image performed by the device for processing the blood vessel image according to the example embodiment can extract a target blood vessel corresponding to main blood vessels from the blood vessel image in which the contrast agent is inserted and automatically identify an error portion without the need to check the error portion in the target blood vessel by inputting manpower. In addition, the device for processing the blood vessel image can automatically correct an error portion identified from the target blood vessel, and to correct the error portion according to the user's intention by receiving the input from the user.

BEST MODE FOR CARRYING OUT THE INVENTION

Figure 1:
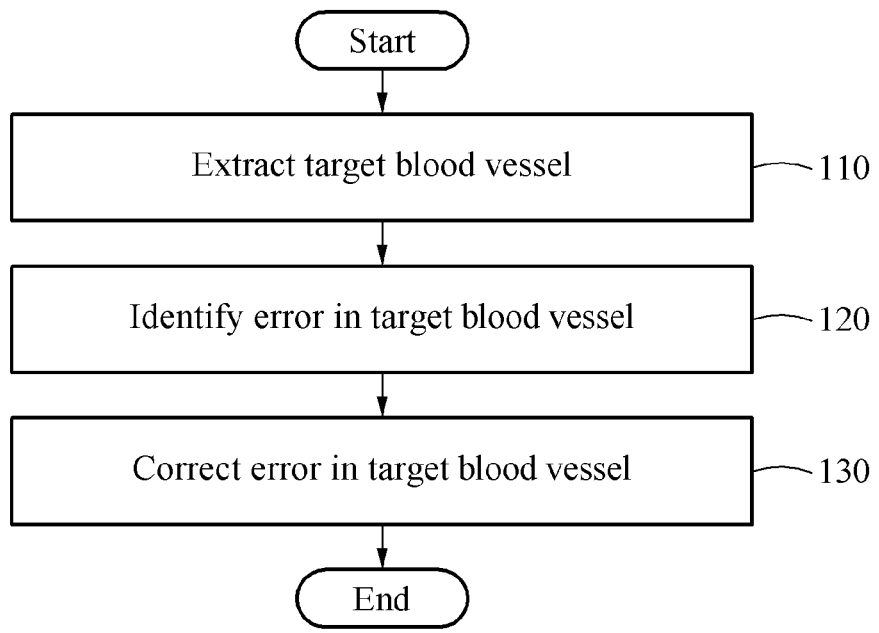
FIG. 1 is a flowchart illustrating a method for processing a blood vessel image according to an example embodiment.

Specific structural or functional descriptions of example embodiments will be disclosed for purposes of only examples and may be changed and implemented in various forms. Accordingly, the example embodiments are not limited to a specific disclosure form, and the scope of the present specification includes changes, equivalents, or substitutes included in the technical spirit.

Terms such as first or second may be used to describe various components, but these terms should be interpreted only for the purpose of distinguishing one component from other components. For example, a first component may be referred to as a second component, and similarly, the second component may be referred to as the first component.

It should be understood that, when it is described that a component is "connected" to the other component, the component may be directly connected to or access the other component, or a third component may be present therebetween.

The singular expression includes the plural expression unless the context clearly dictates otherwise. In the present specification, it should be understood that a term such as "comprise", "have", or the like is intended to designate that a feature, a number, a step, an operation, a component, a part, or a combination thereof described in the specification exists, but it does not preclude the possibility of existence or addition of one or more other features, numbers, steps, operations, components, parts, or combinations thereof.

Unless defined otherwise, all terms used herein, including technical or scientific terms, have the same meaning as those commonly understood by those skilled in the art to which the example embodiments belong. Terms such as those defined in a commonly used dictionary should be interpreted as having a meaning consistent with the meaning in the context of the related art, and should not be interpreted in an ideal or excessively formal meaning unless explicitly defined in the present application. Hereinafter, example embodiments will be described in detail with reference to the accompanying drawings. Like reference numerals illustrated in the respective drawings designate like members.

FIG. 1 is a flowchart illustrating a method for processing a blood vessel image according to an example embodiment.

First, in step 110, the device for processing the blood vessel image may extract a target blood vessel from a blood vessel image. The target blood vessel may also be referred to as a main blood vessel. According to an embodiment, an image receiver of the device for processing the blood vessel image may receive a blood vessel image photographed by a blood vessel image photographing device. The blood vessel image is an image obtained by photographing a blood vessel of a living body and may be generated using a coronary angiography (hereinafter, CAG) image and/or a magnetic resonance imaging (MRI). For example, the blood vessel image may be an image obtained by performing X-ray imaging of a living body into which a contrast agent is injected.

According to an example embodiment, the device for processing the blood vessel image may extract a target blood vessel from the blood vessel image on the basis of a machine learning model. The machine learning model is at least one model having a machine learning structure designed to extract the target blood vessel from the blood vessel image in response to an input of the blood vessel image, and for example, may include a neural network. The device for processing the blood vessel image may calculate an extraction result of the target blood vessel by performing an operation according to the above-described machine learning model on the received blood vessel image. For example, output data of the machine learning model may include a score corresponding to a possibility (e.g., probability) that each pixel in a plurality of pixels of the blood vessel image indicates the target blood vessel. The device for processing the blood vessel image may generate an extraction result of the target blood vessel by determining pixels having a score of a threshold value or more in output data as the target blood vessel. As another example, the output data of the machine learning model is a target blood vessel area segmented from the blood vessel image, and may include pixels extracted as the target blood vessel among the plurality of pixels of the blood vessel image. The extraction result of the target blood vessel may be, for example, a set of pixels extracted as the target blood vessel of pixels of the blood vessel image and/or an image (e.g., a target blood vessel image) corresponding to the target blood vessel area segmented from the blood vessel image.

For reference, the neural network may include a deep neural network (DNN). The DNN may include a fully connected network, a deep convolutional network, a recurrent neural network, and the like. The neural network may perform object classification, object recognition, radar image recognition, and the like by mapping input data and output data in a non-linear relationship to each other based on deep learning. The deep learning is a machine learning technique for solving problems such as object recognition from a big data set and may map input data and output data to each other through supervised or unsupervised learning. In the case of the supervised learning, the aforementioned machine learning model may be trained on the basis of training data including a pair of a training input (e.g., a blood vessel image for training) and a training output (e.g., a ground truth image segmented to the target blood vessel by experts and the like with respect to the blood vessel image for training) mapped in the corresponding training input. For example, the machine learning model may be trained to output the training output from the training input. The machine learning model (hereinafter, a 'temporary model') during training may generate a temporary output in response to the training input, and may be trained so that a loss between the temporary output and the training output (e.g., a ground truth value) is minimized. During the training process, parameters (e.g., connection weights between nodes/layers in the neural network) of the machine learning model may be updated according to the loss.

However, an example in which the machine learning model directly extracts the target blood vessel from the blood vessel image has been described, but the present disclosure is not limited thereto. For example, the machine learning model may include a whole blood vessel extraction model and a target blood vessel extraction model. The whole vessel extraction model may be a model designed to extract a whole blood vessel area from the blood vessel image. The target blood vessel extraction model may be a model designed to extract a target blood vessel area from an image (e.g., a whole blood vessel image) indicating the whole blood vessel area. In addition, instead of the whole vessel extraction model, the device for processing the blood vessel image may also extract the whole blood vessel area by detecting a boundary on the basis of a difference in grayscale level between pixels in the blood vessel image and neighboring pixels. Illustratively, the device for processing the blood vessel image may detect the corresponding pixel as a boundary when a gradient value of grayscale levels of an arbitrary pixel and neighboring pixels is greater than a threshold gradient value. Accordingly, the device for processing the blood vessel image may detect a region in which the grayscale level is rapidly changed as the boundary. The device for processing the blood vessel image may also extract a target blood vessel image using the target blood vessel extraction model from the whole blood vessel image extracted on the basis of the gradient value of the grayscale level.

Furthermore, the device for processing the blood vessel image may also selectively use a machine learning model to be used for extraction of the target blood vessel from among a plurality of machine learning models according to the shape and type of the blood vessel and/or a blood vessel area. According to an example embodiment, the device for processing the blood vessel image may store a plurality of machine learning models for each type of blood vessel (e.g., left main coronary artery (LM), left anterior descending artery (LAD), left circumflex artery (LCX), and right coronary artery (RCA)) and/or for each blood vessel area (e.g., proximal region, mid region, and distal region). For reference, the blood vessel area may be classified into a proximal portion, a middle portion, and a distal portion according to a distance from a blood vessel point into which a catheter is inserted, but is not limited thereto. The blood vessel area may also be classified according to a ratio of a distance from a point where the contrast agent is injected into a blood vessel insertion unit and a distance from a blood vessel end into which the contrast agent may be injected in order to obtain the blood vessel image. For example, the device for processing the blood vessel image may select a type of blood vessel to be extracted and load a machine learning model corresponding to the identified type of blood vessel. The device for processing the blood vessel image may generate an extraction result of a target blood vessel corresponding to the type of blood vessel selected from the blood vessel image using the loaded machine learning model. Illustratively, the device for processing the blood vessel image may store a machine learning model corresponding to a plurality of cardiovascular types (e.g., one right coronary artery and two left coronary arteries). Each of the machine learning models corresponding to the plurality of cardiovascular types may be trained on the basis of training data corresponding to the corresponding cardiovascular type. Trained parameters of the machine learning models for each cardiovascular type may be different from each other, and furthermore, machine learning structures (e.g., convolutional neural networks, U-net structures, etc.) may be different from each other. For convenience of description, the machine learning models in which parameters and/or machine learning structures are distinguished for each type of blood vessel have been described, but the present disclosure is not limited thereto. The device for processing the blood vessel image may also be used for extracting the target blood vessel by storing the plurality of machine learning models that are distinguished from each other by the shape and type of the blood vessel, and/or the blood vessel area and selectively loading a required blood vessel model.

In addition, in step 120, the device for processing the blood vessel image may identify an error portion from the target blood vessel. The error portion may include a discontinuity portion and/or a misidentification portion. The discontinuity portion may indicate a portion where among target blood vessel areas extracted as the target blood vessel and/or pixels indicating the target blood vessel, at least one area and/or at least one pixel is separated or spaced apart from other regions and/or other pixels. The misidentification portion may indicate a portion where an area and/or pixels corresponding to a blood vessel other than the target blood vessel to be actually extracted from the blood vessel image are erroneously extracted as the target blood vessel. Illustratively, the device for processing the blood vessel image may automatically identify an error portion from the extraction result of the target blood vessel on the basis of at least one of blood vessel structure data related to the target blood vessel, curvature information of the target blood vessel, diameter information of the target blood vessel, and brightness information of the target blood vessel. The description of the identification of the error portion will be described below.

Next, in step 130, the device for processing the blood vessel image may correct the identified error portion in response to a case where the error portion is identified in the target blood vessel. The device for processing the blood vessel image may automatically correct the identified error portion, but is not limited thereto. The device for processing the blood vessel image may also correct the error portion on the basis of an input received from a user. The correcting of the error portion will be described below.

Figure 2:
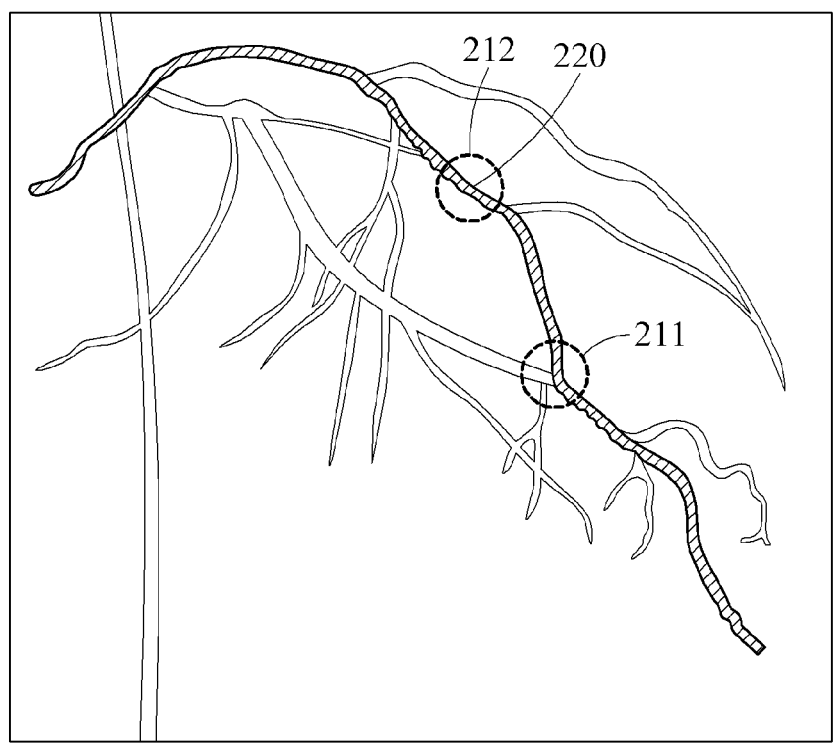
FIG. 2 is a diagram illustrating a blood vessel image in which a target blood vessel is displayed according to an example embodiment.

FIG. 2 is a diagram illustrating a blood vessel image in which a target blood vessel is displayed according to an example embodiment.

A blood vessel image photographing device may photograph a blood vessel image 200. The device for processing the blood vessel image may receive the blood vessel image 200 from the blood vessel image photographing device. The device for processing the blood vessel image may extract a target blood vessel 220 from the received blood vessel image 200. The device for processing the blood vessel image may extract the target blood vessel 220 on the basis of a machine learning model and identify and correct an error portion from an extraction result for the target blood vessel 220. The device for processing the blood vessel image may identify and correct the error portion based on a branch point. The branch point may indicate a point at which two or more blood vessel branches are combined and/or a point at which the blood vessel is divided into a plurality of blood vessel branches. A blood vessel area captured in the blood vessel image 200 may have a plurality of branch points.

Figure 3:
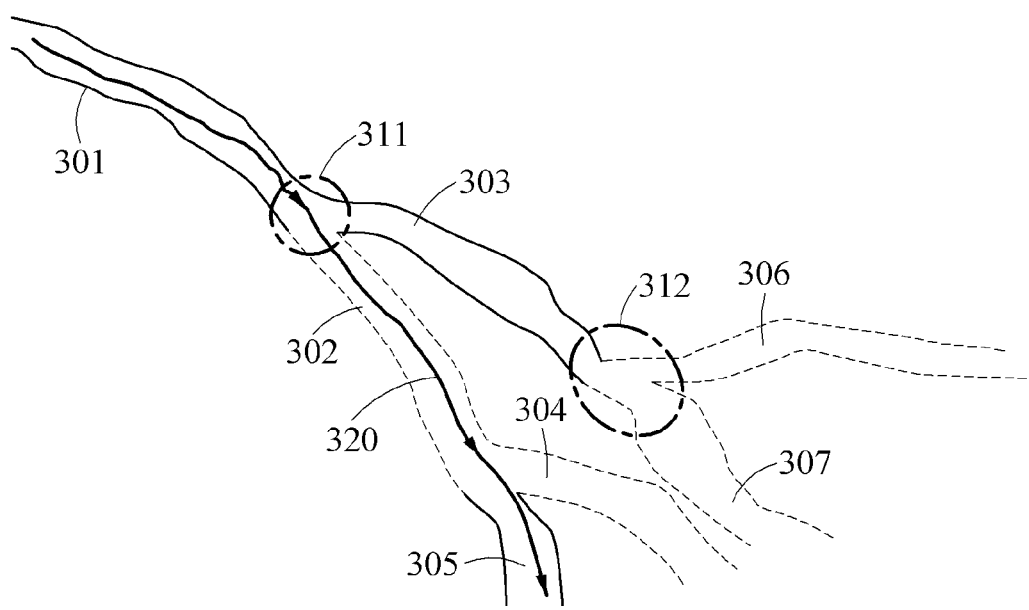
FIG. 3 illustrates an example in which an error portion occurs in an extraction result of the target blood vessel according to an example embodiment.

In order to finally determine the target blood vessel 220 as illustrated in FIG. 2, the device for processing the blood vessel image according to an example embodiment may perform the extraction of the target blood vessel 220 and the identification and correction of the error portion in the extraction result. In FIG. 3 below, for convenience of description, the identification and correction of the error portion according to a method for processing a blood vessel image will be mainly described with respect to a region 211 including the branch point. However, the method for processing the blood vessel image is not applied only to one branch point, but may be applied to one or more branch points (e.g., each of all branch points) in the target blood vessel area indicating the target blood vessel extracted from the blood vessel image. In addition, the device for processing the blood vessel image may identify and correct the error portion not only in a region 211 including the branch point but also in a region 212 without including the branch point.

FIG. 3 illustrates an example in which an error portion occurs in an extraction result of the target blood vessel according to an example embodiment.

The device for processing the blood vessel image according to an example embodiment may identify branch points and branches from the blood vessel image. For example, the device for processing the blood vessel image may extract a whole blood vessel area and identify the branch points and the branches from the extracted whole blood vessel area. The device for processing the blood vessel image may identify blood vessel branches based on the branch point. The whole blood vessel area may be extracted from the blood vessel image. The device for processing the blood vessel image according to an example embodiment may extract the whole blood vessel area from the blood vessel image on the basis of a whole blood vessel extraction model. As described above, the whole blood vessel extraction model may be a model trained to generate output data indicating a result in which the blood vessel area and the remaining non-blood vessel area are divided from the blood vessel image.

FIG. 3 illustrates a portion 300 corresponding to a partial region of the blood vessel image 200 illustrated in FIG. 2 in the extracted whole blood vessel area. The device for processing the blood vessel image may identify blood vessel branches based on the branch points within the partial region. For reference, in the present specification, an upper blood vessel branch may indicate a branch before the branch point according to a progress direction of the blood flow or a progress direction of the contrast agent, a lower blood vessel branch may indicate a branch after the branch point, and a parent blood vessel may indicate the highest branch within the blood vessel area. For example, as a result identified by the device for processing the blood vessel image, first to seventh branches 301 to 307 and branch points 311 and 312 are illustrated. Based on the first branch point 311, the first branch 301 may be an upper blood vessel branch, and the second branch 302 and the third branch 303 may be lower blood vessel branches. In addition, a relationship between the upper blood vessel branch and the lower blood vessel branches is relative, and may vary for each branch point. For example, the second branch 302 may be an upper blood vessel branch with respect to the fourth branch 304 and the fifth branch 305. The device for processing the blood vessel image may generate blood vessel structure data by generating and indexing nodes corresponding to each of the blood vessel branches. The blood vessel structure data will be described below in FIG. 4 below.

In an example illustrated in FIG. 3, the device for processing the blood vessel image may extract the first branch 301, the third branch 303, and the fifth branch 305 as blood vessel branches belonging to the target blood vessel. However, a blood vessel path 320 corresponding to the target blood vessel 220 illustrated in FIG. 2 passes through the first branch 301, the second branch 302, and the fifth branch 305. Accordingly, in the extraction result of the exemplary target blood vessel, the first branch point 311 directed from the first branch 301 to the third branch 303 may be an error portion. The detection and correction of the error portion will be described below.

Figure 4:
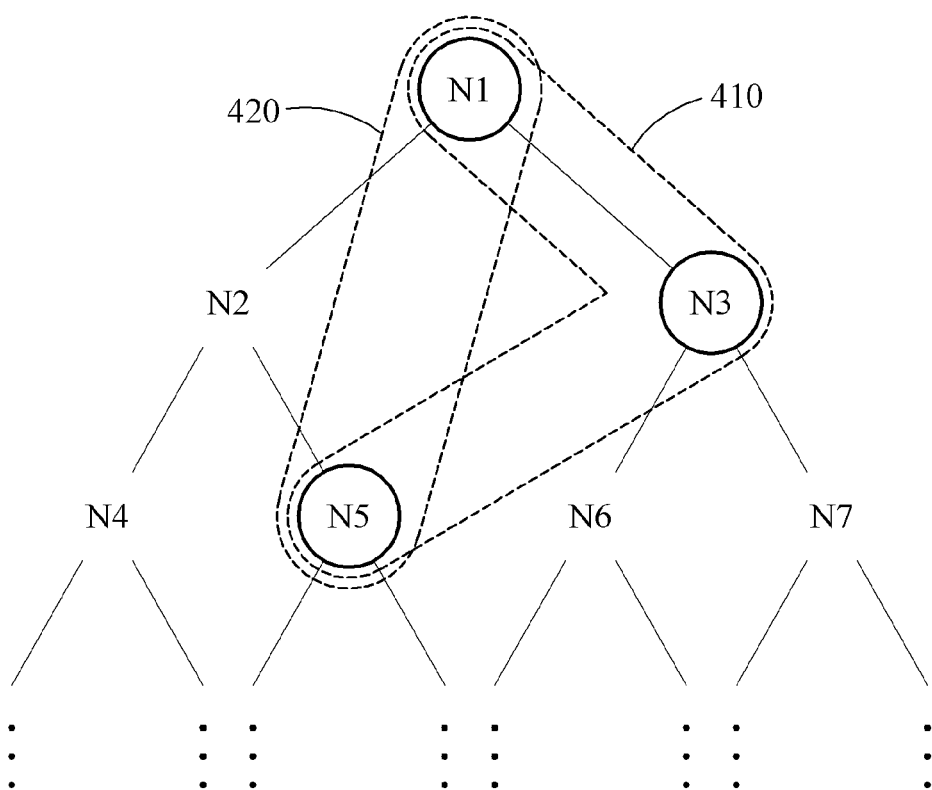
FIG. 4 illustrates a method for identifying an error in a target blood vessel using a topology of blood vessel structure data based on nodes corresponding to blood vessel branches.

FIG. 4 illustrates a method for identifying an error in a target blood vessel using a topology of blood vessel structure data based on nodes corresponding to blood vessel branches.

According to an example embodiment, the device for processing the blood vessel image may identify an error portion on the basis of blood vessel structure data 400 related to the target blood vessel. The blood vessel structure data 400 is topological data indicating the structure of the blood vessel, and may be, for example, tree structure data in which nodes corresponding to blood vessel branches are indexed. For example, the device for processing the blood vessel image may identify blood vessel branches based on blood vessel branch points with respect to the whole blood vessel area, generate nodes corresponding to each of the identified blood vessel branches, and generate the blood vessel structure data 400 on the basis of the indexing of the generated nodes.

When the upper blood vessel branch is branched to a plurality of lower blood vessel branches based on the branch point, the device for processing the blood vessel image may connect the node corresponding to the upper blood vessel branch and the nodes corresponding to the lower blood vessel branches. The device for processing the blood vessel image may generate the blood vessel structure data 400 for the whole blood vessels by repeating the connection of the nodes to the branch points and the vessel blood branches identified from the blood vessel image. For example, in the blood vessel structure data 400 illustrated in FIG. 4, first to seventh nodes N1 to N7 may sequentially correspond to the first to seventh branches 301 to 307 illustrated in FIG. 3, respectively. The first node N1 may be an uppermost node, and the second node N2 and the third node N3 may be lower nodes of the first node N1. The remaining nodes may have similar top-down relationships.

The device for processing the blood vessel image according to an example embodiment may calculate node connection data 410 between the nodes corresponding to the blood vessel branches extracted as the target blood vessel from the blood vessel image. For example, the device for processing the blood vessel image may calculate the node connection data 410 connected with the first node N1, the third node N3, and the fifth node N5 from the extraction result of the target blood vessel illustrated in FIG. 3.

The device for processing the blood vessel image may identify an error portion of the target blood vessel by comparing the node connection data 410 with the blood vessel structure data 400. The device for processing the blood vessel image may detect a connection error between the nodes of the target blood vessel on the basis of the generated blood vessel structure data 400. The device for processing the blood vessel image may determine, as an error portion, blood vessel branches and/or branch points corresponding to the nodes in which the connection error is detected. The device for processing the blood vessel image may determine an error portion on the basis of nodes which are not matched with the blood vessel structure data 400 in the node connection data 410. Illustratively, the node connection data 410 extracted in FIG. 4 may indicate that the first node N1, the third node N3, and the fifth node N5 are sequentially connected. In the blood vessel structure data 400, the third node N3 is not connected to the fifth node N5. In other words, the device for processing the blood vessel image may determine that the connection between the third node N3 and the fifth node N5 in the node connection data 410 does not match the blood vessel structure data 400. The connection between the third node N3 and the fifth node N5 may be a connection error. The device for processing the blood vessel image may determine a blood vessel branch corresponding to at least one node of the nodes corresponding to the connection error as the error portion. For example, in FIG. 4, the device for processing the blood vessel image may determine a blood vessel branch corresponding to at least one of the third node N3 and the fifth node N5 as the error portion. In the above-described example, since the blood vessel branch corresponding to the third node N3 or the fifth node N5 is erroneously extracted as the target blood vessel, the blood vessel branch may be a misidentification portion.

As another example, the device for processing the blood vessel image may detect the blood vessel branch corresponding to a node missing from the node connection data 420 as a discontinuity portion on the basis of the blood vessel structure data 400. The device for processing the blood vessel image may calculate the node connection data 420 directly connected from the first node N1 to the fifth node N5. The device for processing the blood vessel image may detect that the second node N2 is missing from the node connection data 420 on the basis of the blood vessel structure data 400. In this case, the device for processing the blood vessel image may detect a blood vessel branch corresponding to the second node N2 as the discontinuity portion.

Figure 5:
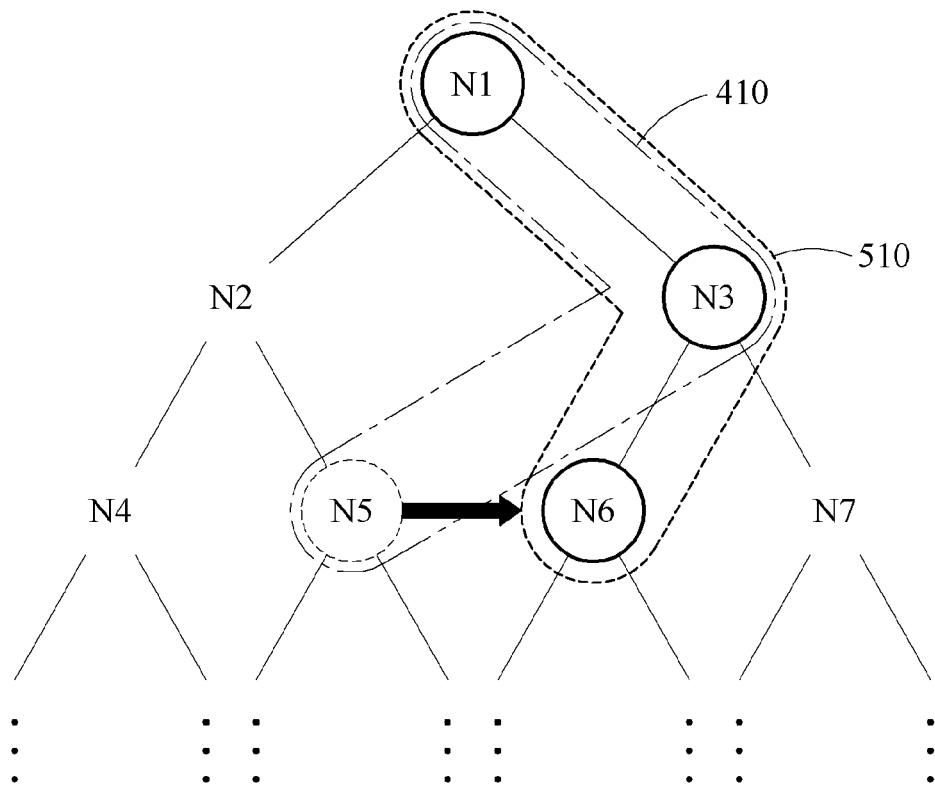
FIGS. 5 and 6 illustrate a method for correcting an error portion according to an example embodiment.
Figure 6:
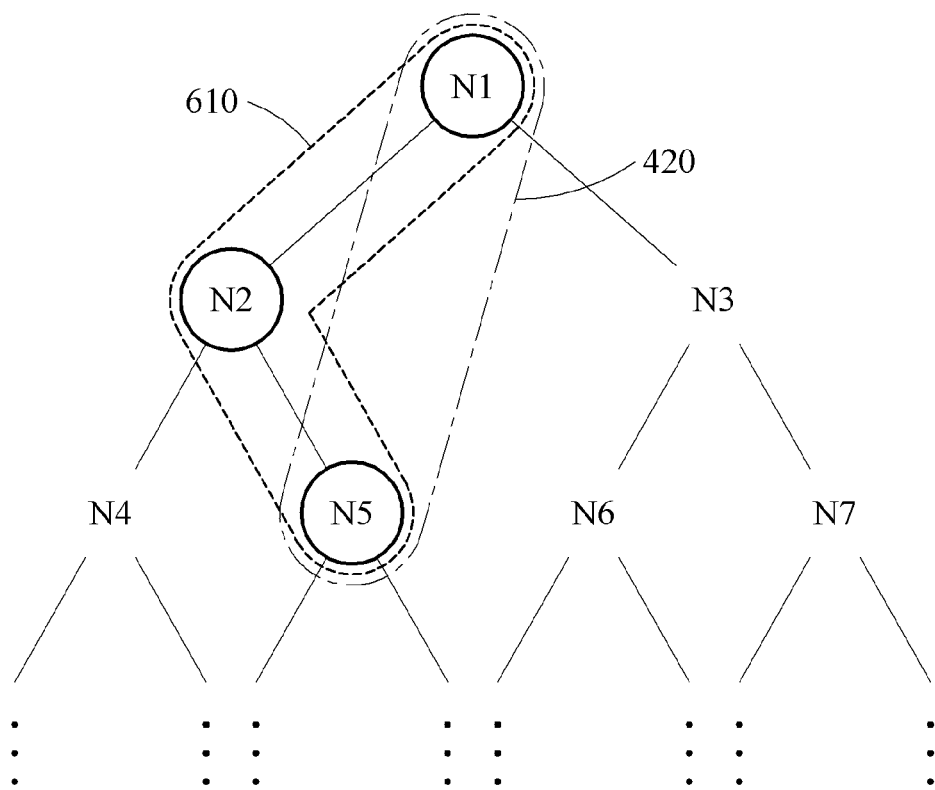

FIGS. 5 and 6 illustrate a method for correcting an error portion according to an example embodiment.

FIG. 5 illustrates a correction in the case where the node connection data 410 is calculated in FIG. 4. According to an example embodiment, in response to a case where the misidentification portion is identified, the device for processing the blood vessel image may replace a node corresponding to the misidentification portion with a node matching the blood vessel structure data. Illustratively, the device for processing the blood vessel image may determine that the fifth node N5 does not match the blood vessel structure data in the node connection data 410. The device for processing the blood vessel image may exclude the fifth node N5 that does not match the blood vessel structure data from the node connection data and add the sixth node N6 matching the blood vessel structure data to the node connection data to generate corrected node connection data 510. Accordingly, the device for processing the blood vessel image may extract a blood vessel branch (e.g., a sixth branch 306 in FIG. 6) corresponding to the replaced sixth node N6 as the target blood vessel.

FIG. 6 illustrates a correction when the node connection data 420 is calculated in FIG. 4. According to an example embodiment, the device for processing the blood vessel image may connect regions corresponding to the discontinuity portion in response to a case where the discontinuity portion is identified. For example, the device for processing the blood vessel image may insert a connectable node between the nodes corresponding to the discontinuity portion. For example, the device for processing the blood vessel image may determine that a space between the first node N1 and the fifth node N5 is missing from the node connection data 420. The device for processing the blood vessel image may generate corrected node connection data 610 by inserting the second node N2 between the nodes N1 and N5. The device for processing the blood vessel image may extract a blood vessel branch (e.g., the second branch 302 in FIG. 3) corresponding to the second node N2 as the target blood vessel. As another example, the device for processing the blood vessel image may correct the connecting of the regions corresponding to nodes corresponding to the discontinuity portion. Although it is illustrated in FIG. 4 that the first node N1, the second node N2, and the fifth node N5 are sequentially connected, the present disclosure is not limited thereto. The first node N1 and the fifth node N5 may be connected, and the region corresponding to the first node N1 and the region corresponding to the fifth node N5 may also be discontinued. In the device for processing the blood vessel image, when the region corresponding to the first node N1 and the region corresponding to the fifth node N5 are discontinued, the region corresponding to the first node N1 and the fifth node N5 may be naturally connected so as not be separated.

As described above, by correcting the misidentification portion by replacing the nodes and adding the nodes, the device for processing the blood vessel image may remove a node connectivity error based on a topology of the blood vessel structure data.

Figure 7:
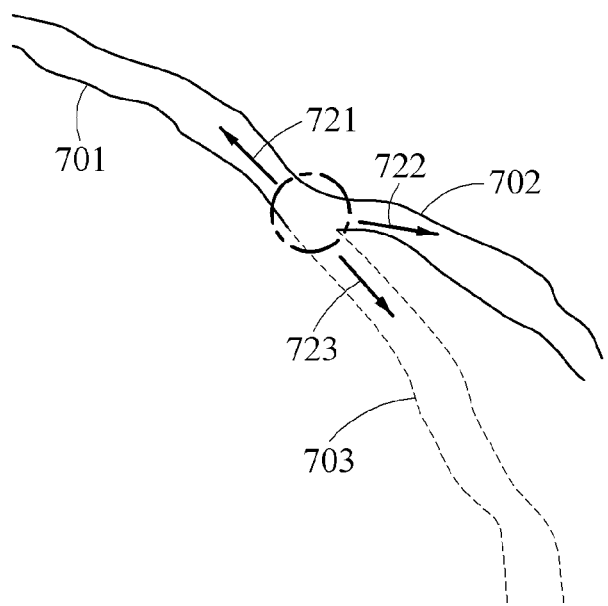
FIG. 7 illustrates a method for identifying and correcting an error in a target blood vessel using curvature information of the target blood vessel.

FIG. 7 illustrates a method for identifying and correcting an error in a target blood vessel using curvature information of the target blood vessel.

According to an example embodiment, the device for processing the blood vessel image may identify and correct a misidentification portion by using a curvature between an upper branch and a lower branch adjacent to each other based on a branch point in the target blood vessel. For example, the device for processing the blood vessel image may determine a lower branch as a misidentification portion in response to a case where a curvature between the upper branch and the lower branch adjacent to each other based on the branch point in the target blood vessel exceeds a threshold curvature. For example, when the device for processing the blood vessel image first extracts blood vessel branches 701 and 702 as a target blood vessel, the device for processing the blood vessel image may calculate a curvature between the blood vessel branches 701 and 702. The device for processing the blood vessel image may determine the lower blood vessel branch 702 of the above-described blood vessel branches 701 and 702 as the misidentification portion in the extraction result for the target blood vessel in response to a case where the calculated curvature exceeds the threshold curvature. A relatively small curvature is shown between the upper blood vessel branch and the lower blood vessel branch adjacent to each other in the target blood vessel to be actually extracted from the blood vessel image. Accordingly, there is a possibility that the upper blood vessel branch and the lower blood vessel branch adjacent to each other having a curvature exceeding the threshold curvature may include the error portion.

The device for processing the blood vessel image may correct the identified error portion in response to a case where the error portion is identified in the target blood vessel using the threshold curvature. The device for processing the blood vessel image may replace the lower branch of the upper branch and the lower branch divided based on the branch point including the error portion in the target blood vessel with a candidate lower branch having a curvature with the branch of the threshold curvature or less, with respect to the identified error portion. The candidate lower branch may represent one or more remaining lower branches that are not extracted as the target blood vessel among a plurality of lower blood vessel branches connected to one blood vessel branch based on an arbitrary branch point.

Illustratively, when the curvature between the upper blood vessel branch 701 and the candidate lower blood vessel branch 703 which is not extracted as the target blood vessel is the threshold curvature or less, the device for processing the blood vessel image may extract the candidate lower blood vessel branch 703 instead of the lower blood vessel branch 702 as the target blood vessel. The device for processing the blood vessel image may replace the lower blood vessel branch 702 as the candidate lower blood vessel branch 703 in the extraction result of the target blood vessel. Furthermore, when correcting the identified error portion, the device for processing the blood vessel image may apply a different threshold curvature according to a type of blood vessel (e.g., left main coronary artery (LM), left anterior descending artery (LAD), left circumflex artery (LCX), and right coronary artery (RCA)) or a blood vessel area (e.g., proximal region, mid region, and distal region).

The device for processing the blood vessel image may perform principal direction component analysis (e.g., principal component analysis (PCA)) of the blood vessel branch in order to analyze a difference in curvature. The device for processing the blood vessel image may analyze a principal direction component for each of the blood vessel branches divided based on the branch point. The principal direction component of the blood vessel branch may represent a component representing a direction of the corresponding blood vessel branch. For example, the device for processing the blood vessel image may obtain a principal direction vector for each of the blood vessel branches by using the principal direction component analysis for each of the blood vessel branches. The principal direction vector is a vector having a direction component representing a direction in which the blood vessel branch extends from the branch point, and may have a size of a unit vector. For example, the principal direction vector for any blood vessel branch may indicate a direction of the principal components of vector components directed from the branch point to points corresponding to the blood vessel branch. Illustratively, the principal direction vectors of the blood vessel branches 701, 702, and 703 may correspond to vectors 721, 722, and 723, respectively. The device for processing the blood vessel image may determine a lower branch as a misidentification portion in response to a case where an inner product value of the principal direction vector between the upper branch and the lower branch based on the branch point in the target blood vessel exceeds a threshold value.

Illustratively, when inner product values of the principal direction vectors 721 and 722 of the upper branch 701 and the lower branch 702 in the target blood vessel exceed a threshold value, the device for processing the blood vessel image may determine that the upper branch 701 and the lower branch 702 include the misidentification portion. Since the principal direction vector of each of the blood vessel branches has the size of the unit vector, the inner product values of the principal direction vectors may depend on angles formed between the vectors. As a result, since the principal direction vector corresponding to the upper branch and the principal direction vector corresponding to the lower branch are directed in opposite directions, the inner product of the two principal direction vectors has a negative value. Accordingly, when the inner product values of the principal direction vectors are a threshold value or more, it may be meant that the curvature between the blood vessel branches is large. The target blood vessel to be actually extracted from the blood vessel image is one blood vessel and has generally no large curvature change between the upper blood vessel branch and the lower blood vessel branch adjacent to each other. Accordingly, when the inner product value of the principal direction vector between the upper blood vessel branch and the lower blood vessel branch adjacent to each other exceeds the threshold value, the device for processing the blood vessel image may extract blood vessels other than the target blood vessel to be actually found. Furthermore, in the correcting of the identified error portion, the device for processing the blood vessel image may apply different threshold values according to a type of blood vessel or a blood vessel area.

The device for processing the blood vessel image may obtain a principal direction vector for each blood vessel branch segmented based on the branch point with respect to the extracted target blood vessel, but may also obtain a principal direction vector for each piece segmented in a predetermined length by segmenting the blood vessel in the predetermined length. The device for processing the blood vessel image may also identify an error portion in the target blood vessel by comparing principal directions of an upper piece and a lower piece with respect to the extracted target blood vessel to find a portion in which the curvature is greater than or equal to a threshold value. The upper piece and the lower piece may be defined according to a progress direction of the blood flow or a progress direction of the contrast agent. In other words, the device for processing the blood vessel image may segment the extracted target blood vessel in a threshold length or less. The device for processing the blood vessel image may determine one of the upper piece and the lower piece adjacent to each other as a misidentification portion in response to a case where inner product values of principal direction vectors of the upper piece and the lower piece adjacent to each other segmented in the predetermined length exceed the threshold value. Since the device for processing the blood vessel image may calculate a curvature between the upper piece and the lower piece by segmenting the target blood vessel in a threshold length or less, the device for processing the blood vessel image may identify the error portion of the target blood vessel more accurately than a case of identifying the error portion of the target blood vessel according to the blood vessel branches segmented based on the branch point.

The device for processing the blood vessel image may correct the identified error portion in response to a case where the error portion is identified in the target blood vessel using the principal direction vector. The device for processing the blood vessel image may replace the lower branch of the upper branch and the lower branch divided based on the branch point including the error portion in the target blood vessel with a candidate lower branch having an inner product value of the principal direction vector with the branch of the threshold value or less, with respect to the identified error portion.

Illustratively, when inner product values of principal direction vectors 723 and 721 between the upper blood vessel branch 701 and the candidate lower blood vessel branch 703 which is not extracted as the target blood vessel is the threshold value or less, the device for processing the blood vessel image may extract the candidate lower blood vessel branch 703 instead of the lower blood vessel branch 702 as the target blood vessel. The device for processing the blood vessel image may replace the lower blood vessel branch 702 as the candidate lower blood vessel branch 703 in the extraction result of the target blood vessel.

Figure 8:
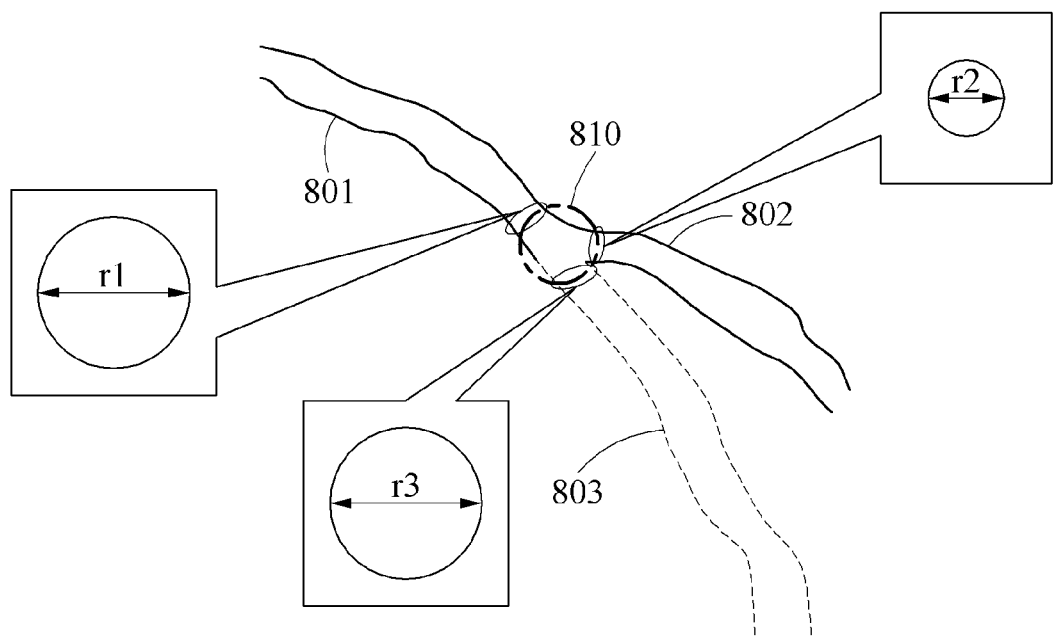
FIG. 8 illustrates a method for identifying and correcting an error in a target blood vessel using diameter information of the target blood vessel.

FIG. 8 illustrates a method for identifying and correcting an error in a target blood vessel using diameter information of the target blood vessel.

According to an example embodiment, the device for processing the blood vessel image may identify and correct a misidentification portion by calculating a diameter difference between the upper branch and the lower branch adjacent to each other based on the branch point in the target blood vessel. According to an example embodiment, the device for processing the blood vessel image may determine a lower branch as a misidentification portion in response to a case where a diameter difference between the upper branch and the lower branch adjacent to each other based on the branch point in the target blood vessel is a threshold or more. The device for processing the blood vessel image may acquire diameter information with respect to each of the blood vessel branches identified based on the branch points on the basis of a model ensemble. For example, diameters of blood vessel branches 801, 802, and 803 illustrated in FIG. 8 may correspond to r1, r2, and r3, respectively. Illustratively, when the device for processing the blood vessel image first extracts the blood vessel branches 801 and 802 as a target blood vessel, the device for processing the blood vessel image may calculate a diameter difference between the blood vessel branches 801 and 802. The device for processing the blood vessel image may determine at least one branch of the above-described blood vessel branches 801 and 802 as the misidentification portion in the extraction result for the target blood vessel in response to a case where the calculated diameter difference is a threshold diameter difference or more. A relatively small diameter difference is shown between the upper blood vessel branch and the lower blood vessel branch adjacent to each other in the target blood vessel to be actually extracted from the blood vessel image. Accordingly, there is a possibility that the upper blood vessel branch and the lower blood vessel branch adjacent to each other having a diameter difference of the threshold diameter difference or more may include the error portion. According to another example embodiment, the device for processing the blood vessel image may determine the diameter information acquired for the upper branch and the lower branch adjacent to each other as an error, in response to a case where the diameter difference between the upper branch and the lower branch adjacent to each other in the target blood vessel is a threshold diameter difference or more. In other words, when the diameter difference between the upper branch and the lower branch adjacent to each other based on the branch point in the target blood vessel is the threshold diameter difference or more, the device for processing the blood vessel image may identify one of the upper branch and the lower branch adjacent to each other as an error portion and determine that diameter information about at least one blood vessel branch of the upper branch and the lower branch is erroneous. That is, the device for processing the blood vessel image may erroneously predict a diameter larger than or smaller than the actual diameter of the blood vessel branch, with respect to at least one of the upper branch and the lower branch adjacent to each other. Illustratively, when the device for processing the blood vessel image first extracts the blood vessel branches 801 and 802 as the target blood vessel, the device for processing the blood vessel image may determine that the diameter for at least one branch of the blood vessel branches 801 and 802 is erroneously predicted.

The device for processing the blood vessel image may calculate a diameter difference between the upper vessel branch and the lower blood vessel branch adjacent to each other with respect to the extracted target blood vessel, but may also calculate the diameter difference by smoothing the diameter information of the blood vessel branches. It is general to represent a relatively small change in diameter between the upper branch and the lower branch adjacent to each other in the target blood vessel to be actually extracted from the blood vessel image. However, when the target blood vessel to be extracted includes a blood vessel branch having a disease, a large change in diameter may occur between blood vessel branches connected with the blood vessel branch having the disease. Accordingly, the device for processing the blood vessel image may identify a misidentification portion in the extracted target blood vessel by smoothing the diameter information of blood vessel branches by binding the plurality of blood vessel branches to calculate a diameter difference.

The device for processing the blood vessel image may correct the identified error portion in response to a case where the error portion is identified in the target blood vessel using the diameter information. The device for processing the blood vessel image may correct the identified error portion by performing at least one of replacing the lower branch based on the diameter difference from the upper branch with respect to the identified error portion and generating a new extraction result including new diameter information about the target blood vessel.

The device for processing the blood vessel image according to an example embodiment may replace a lower branch divided based on the branch point including the misidentification portion with a candidate lower branch in which the diameter difference from the upper branch is less than a threshold, with respect to the identified misidentification portion. It is general that the diameter of the blood vessel is decreased according to the progress direction of the blood flow or the progress direction of the contrast agent. Accordingly, the device for processing the blood vessel image according to an example embodiment may replace the lower branch with a candidate lower branch having a smaller diameter than the upper branch and having a diameter difference from the upper branch of less than the threshold diameter difference. Illustratively, when the diameter difference between the upper blood vessel branch 801 and the candidate blood vessel branch 803 which is not extracted as the target blood vessel is less than the threshold diameter difference, the device for processing the blood vessel image may extract the candidate blood vessel branch 803 instead of the lower blood vessel branch 802 as the target blood vessel. The device for processing the blood vessel image may replace the lower blood vessel branch 802 with the candidate lower blood vessel branch 803 in the extraction result of the target blood vessel.

As another example, the device for processing the blood vessel image may determine the diameter information acquired for at least one of the upper branch and the lower branch adjacent to each other as an error, in response to a case where the diameter difference between the upper branch and the lower branch adjacent to each other in the target blood vessel is the threshold diameter difference or more. When the diameter information acquired for the target blood vessel is determined as the error, the device for processing the blood vessel image may generate a new extraction result for the target blood vessel. That is, the device for processing the blood vessel image may determine that a diameter is expected to be larger or smaller than the actual diameter of the blood vessel branch, with respect to at least one of the upper branch and the lower branch adjacent to each other. The device for processing the blood vessel image may generate a new extraction result including new diameter information with respect to the target blood vessel on the basis of the model ensemble distinguished from the model ensemble applied in the previous extraction result in order to obtain the new diameter information for the target blood vessel. Furthermore, the device for processing the blood vessel image can also obtain new diameter information for the whole blood vessel, but can correct newly only the new diameter information for the blood vessel branches in which the diameter information is determined as the error. When correcting the identified error portion, the device for processing the blood vessel image may apply a different threshold diameter difference according to a type of blood vessel (e.g., LM, LAD, LCX, and RCA) or a blood vessel area.

Figure 9:
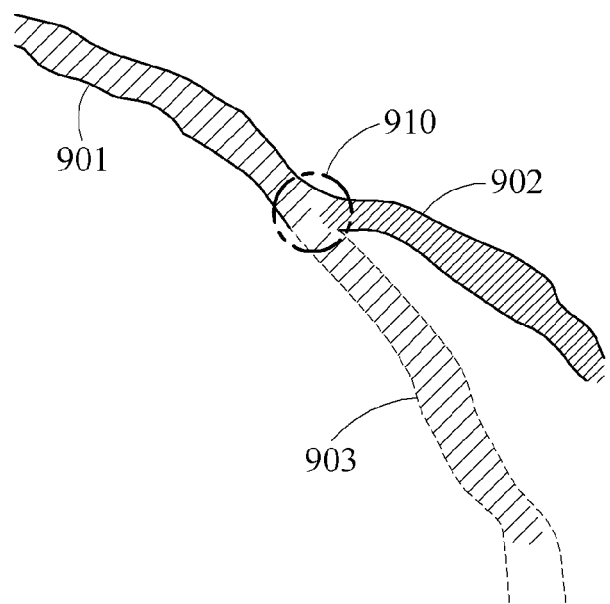
FIG. 9 illustrates a method for identifying and correcting an error in a target blood vessel using brightness information of the target blood vessel.

FIG. 9 illustrates a method for identifying and correcting an error in a target blood vessel using brightness information of the target blood vessel.

According to an example embodiment, the device for processing the blood vessel image may identify and correct a misidentification portion by calculating a brightness difference between the upper branch and the lower branch adjacent to each other based on the branch point in the target blood vessel. For example, the device for processing the blood vessel image may determine a lower branch as a misidentification portion, in response to a case where the brightness difference between the upper branch and the lower branch adjacent to each other based on the branch point in the target blood vessel is a threshold brightness difference or more. The device for processing the blood vessel image may acquire brightness information with respect to each of the blood vessel branches identified based on the branch points on the basis of a model ensemble. For example, the brightness of the blood vessel branches may indicate a distribution concentration of a contrast agent injected to obtain a blood vessel image. Illustratively, when the device for processing the blood vessel image first extracts blood vessel branches 901 and 902 as a target blood vessel, the device for processing the blood vessel image may calculate a brightness difference between the blood vessel branches 901 and 902. The device for processing the blood vessel image may determine the lower blood vessel branch 902 of the above-described blood vessel branches 901 and 902 as the misidentification portion in the extraction result for the target blood vessel in response to a case where the calculated brightness difference is the threshold brightness difference or more. A relatively small change in brightness is shown between the upper blood vessel branch and the lower blood vessel branch adjacent to each other in the target blood vessel to be actually extracted from the blood vessel image. Accordingly, there is a possibility that the upper blood vessel branch and the lower blood vessel branch adjacent to each other having a brightness difference of the threshold brightness difference or more may include the error portion. According to another example embodiment, the device for processing the blood vessel image may determine the brightness information acquired for the upper branch and the lower branch adjacent to each other as an error, in response to a case where the brightness difference between the upper branch and the lower branch adjacent to each other in the target blood vessel is the threshold brightness difference or more. In other words, when the brightness difference between the upper branch and the lower branch adjacent to each other based on the branch point in the target blood vessel is the threshold brightness difference or more, the device for processing the blood vessel image may identify one of the upper branch and the lower branch adjacent to each other as an error portion and determine that brightness information about at least one blood vessel branch of the upper branch and the lower branch is erroneous. That is, the device for processing the blood vessel image may erroneously predict brightness brighter or darker than the actual brightness of the blood vessel branch, with respect to at least one blood vessel branch of the upper branch and the lower branch adjacent to each other. Illustratively, when the device for processing the blood vessel image first extracts the blood vessel branches 901 and 902 as the target blood vessel, the device for processing the blood vessel image may determine that the diameter for at least one branch of the aforementioned blood vessel branches 901 and 902 is erroneously predicted.

The device for processing the blood vessel image may correct the identified error portion in response to a case where the error portion is identified in the target blood vessel using the brightness information. According to an example embodiment, the device for processing the blood vessel image may determine a lower blood vessel branch as a misidentification portion in response to a case where the brightness difference between the upper blood vessel branch and the lower blood vessel branch adjacent to each other in the target blood vessel is the threshold brightness difference or more. The device for processing the blood vessel image may replace the lower branch with a candidate lower branch having a brightness difference from the upper branch of less than the threshold brightness difference with respect to the identified misidentification portion. Illustratively, when the brightness difference between the upper blood vessel branch 901 and the candidate lower blood vessel branch 903 which is not extracted as the target blood vessel is less than the threshold brightness difference, the device for processing the blood vessel image may extract the candidate lower blood vessel branch 903 instead of the lower blood vessel branch 902 as the target blood vessel. The device for processing the blood vessel image may replace the lower blood vessel branch 902 with the candidate lower blood vessel branch 903 in the extraction result of the target blood vessel. Furthermore, when correcting the identified error portion, the device for processing the blood vessel image may apply a different threshold brightness difference according to a type of blood vessel (e.g., LM, LAD, LCX, and RCA) or a blood vessel area.

According to another example embodiment, the device for processing the blood vessel image may determine the brightness information acquired for at least one of the upper branch and the lower branch adjacent to each other as an error, in response to a case where the brightness difference between the upper branch and the lower branch adjacent to each other in the target blood vessel is the threshold brightness difference or more. When the brightness information acquired for the target blood vessel is determined as the error, the device for processing the blood vessel image may generate a new extraction result for the target blood vessel. That is, the device for processing the blood vessel image may determine that brightness is expected to be brighter or darker than the actual brightness of the blood vessel branch, with respect to at least one blood vessel branch of the upper branch and the lower branch adjacent to each other. The device for processing the blood vessel image may generate a new extraction result including new diameter information with respect to the target blood vessel on the basis of the model ensemble distinguished from the model ensemble applied in the previous extraction result in order to obtain the new brightness information for the target blood vessel. Furthermore, the device for processing the blood vessel image can also obtain new brightness information for the whole blood vessel, but can correct newly only the new brightness information for the blood vessel branches in which the brightness information is determined as the error.

The device for processing the blood vessel image according to an example embodiment may identify and correct the error portion not only in a region including the branch points but also in a region without including the branch points. For example, the device for processing the blood vessel image may correct the error portion occurring within one blood vessel branch. A region corresponding to one blood vessel branch may represent a discontinuity portion which is a separated or spaced region other than a spatially connected region. When a region corresponding to one blood vessel branch is discontinued, the device for processing the blood vessel image may perform a correction of naturally connecting regions corresponding to one blood vessel branch so as not to be separated from each other. As another example, when a change in diameter of the blood vessel within one vessel branch is a threshold diameter or more, the device for processing the blood vessel image may determine the diameter information of the blood vessel branch as an error and correct new diameter information about the blood vessel branch to be newly obtained. Similarly, when a change in brightness of the blood vessel within one blood vessel branch is the threshold brightness or more, the device for processing the blood vessel image may determine the brightness information of the blood vessel branch as an error and correct new brightness information about the blood vessel branch to be newly obtained.

The device for processing the blood vessel image according to an example embodiment may generate a new extraction result for the target blood vessel on the basis of the model ensemble distinguished from the model ensemble applied in the previous extraction result, in response to a case where the error portion is identified. When the error portion is identified, the device for processing the blood vessel image may generate a new extraction result for the target blood vessel on the basis of one model ensemble distinguished from the model ensemble applied in the previous extraction result among a plurality of stored machine learning models without directly correcting the error portion.

In addition, the device for processing the blood vessel image may generate an extraction result for the target blood vessel on the basis of two or more model ensembles among a plurality of stored machine learning models, respectively. The device for processing the blood vessel image may identify an error portion every extraction result of the target blood vessel generated according to the model ensemble on the basis of at least one of blood vessel structure data related to the target blood vessel, curvature information of the target blood vessel, diameter information of the target blood vessel, and brightness information of the target blood vessel. The device for processing the blood vessel image may automatically select one extraction result closest to the target blood vessel to be actually extracted among generated extraction results for the plurality of target blood vessels as a target blood vessel. For example, the device for processing the blood vessel image may select an extraction result for a target blood vessel with the smallest identified error portion as the extraction result closest to the target blood vessel to be actually extracted, but is not limited thereto. Furthermore, the device for processing the blood vessel image may provide information on the extraction results for the plurality of target blood vessels to the user. The device for processing the blood vessel image may receive one of the extraction results for the plurality of target blood vessels from the user to select the received extraction result as the target blood vessel.

The device for processing the blood vessel image according to an example embodiment may extract one blood vessel branch of candidate blood vessel branches as the target blood vessel on the basis of a connectivity score for each of the candidate blood vessel branches in response to a case where the error portion is identified in the extraction result of the target blood vessel. When the error portion is identified in the extraction result of the target blood vessel, the device for processing the blood vessel image may select one blood vessel branch of the candidate blood vessel branches capable of correcting the error portion. The device for processing the blood vessel image may calculate a connectivity score for each of the candidate blood vessel branches. The connectivity score is a score indicating the connectivity between a blood vessel branch connected with any candidate blood vessel branch and the corresponding candidate blood vessel branch in the extraction result of the target blood vessel. For example, the connectivity score may be calculated on the basis of a degree of matching, a curvature difference, a diameter difference, a brightness difference, etc. for blood vessel structure data between the candidate blood vessel branch and the blood vessel branch connected to the candidate blood vessel branch. The connectivity score may correspond to a degree similar to the target blood vessel to be actually extracted from the corrected target blood vessel when the candidate blood vessel branch is included as the target blood vessel.

For example, when the candidate blood vessel branch is extracted as the target blood vessel, the device for processing the blood vessel image may calculate a connectivity score between the candidate blood vessel branch and the blood vessel branches connected to the candidate blood vessel branch on the basis of at least one of the blood vessel structure data related to the target blood vessel, the curvature information of the target blood vessel, the diameter information of the target blood vessel, and the brightness information of the target blood vessel. However, the present disclosure is not limited thereto, and the connectivity score for each of the candidate blood vessel branches may be calculated using various methods. The device for processing the blood vessel image may select one blood vessel branch of the candidate blood vessel branches on the basis of the connectivity score. For example, as a blood vessel branch having the highest connectivity score among the candidate blood vessel branches, a blood vessel branch determined to have the smallest error may be selected. The device for processing the blood vessel image may extract the selected blood vessel branch as the target blood vessel.

Illustratively, in FIG. 5, when the device for processing the blood vessel image calculates the node connection data 410 to which the first node N1, the third node N3, and the fifth node N5 are connected from the extraction result of the target blood vessel, the device for processing the blood vessel image may determine that the connection between the third node N3 and the fifth node N5 in the node connection data 410 does not match the blood vessel structure data 400. The device for processing the blood vessel image may determine a blood vessel branch corresponding to at least one node of the nodes N3 and N5 corresponding to the connection error as the error portion. When the device for processing the blood vessel image determines the blood vessel branch corresponding to the third node N3 as the error, the device for processing the blood vessel image may exclude the third node N3 which does not match the blood vessel structure data from the node connection data and add the second node N2 matching the blood vessel structure data to the node connection data. In addition, when the device for processing the blood vessel image determines the blood vessel branch corresponding to the fifth node N5 as the error, the device for processing the blood vessel image may exclude the fifth node N5 which does not match the blood vessel structure data from the node connection data and add a sixth node N6 or a seventh node N7 matching the blood vessel structure data to the node connection data. As a result, the device for processing the blood vessel image may calculate a connectivity score for each of candidate blood vessel branches corresponding to the second node, the sixth node, and the seventh node that may be nodes of the target blood vessel. The device for processing the blood vessel image may select a blood vessel branch determined to have the smallest error to extract the selected blood vessel branch as the target blood vessel, on the basis of the connectivity score for each of the candidate blood vessel branches.

As another example, in FIG. 7, when the device for processing the blood vessel image first extracts the blood vessel branches 701 and 702 as the target blood vessel, the device for processing the blood vessel image may determine the blood vessel branches as an error portion when a curvature between the blood vessel branches 701 and 702 exceeds a threshold curvature. The device for processing the blood vessel image may replace a lower branch of the upper branch and the lower branch adjacent to each other with a candidate lower branch having a curvature with the upper branch of the threshold curvature or less. Unlike illustrated in FIG. 7, when there is a plurality of candidate lower blood vessel branches, the device for processing the blood vessel image may calculate a connectivity score for each of the candidate blood vessel branches. The device for processing the blood vessel image may select a blood vessel branch determined to have the smallest error to extract the selected blood vessel branch as the target blood vessel, on the basis of the connectivity score for each of the candidate blood vessel branches. Even in FIGS. 8 and 9, the device for processing the blood vessel image may select and extract one of the candidate blood vessel branches as the target blood vessel in the same manner as described above.

Figure 10:
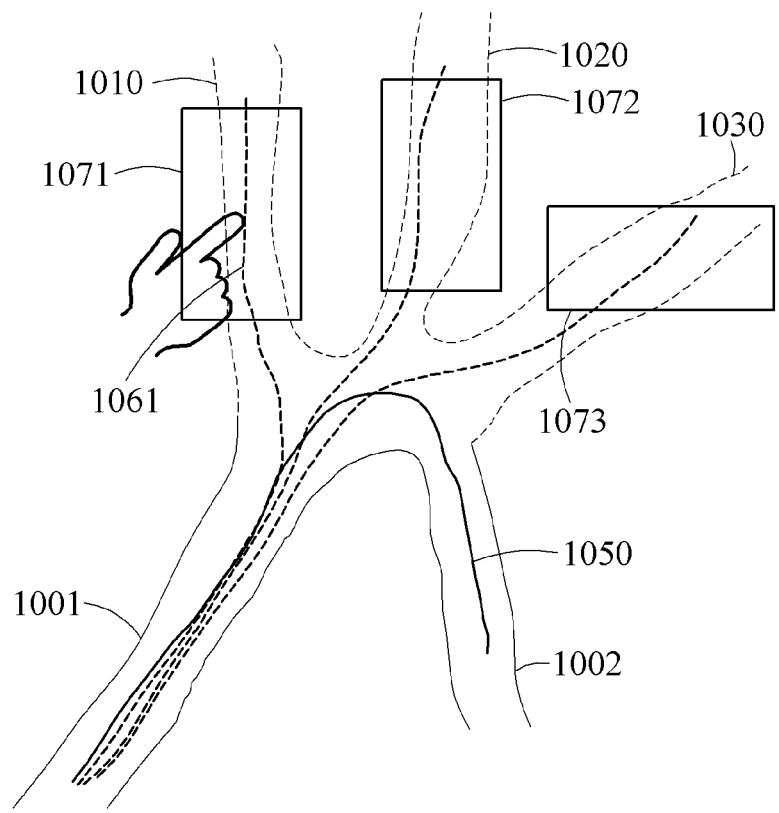
FIGS. 10 and 11 illustrate a method for correcting an error portion according to an example embodiment.
Figure 11:
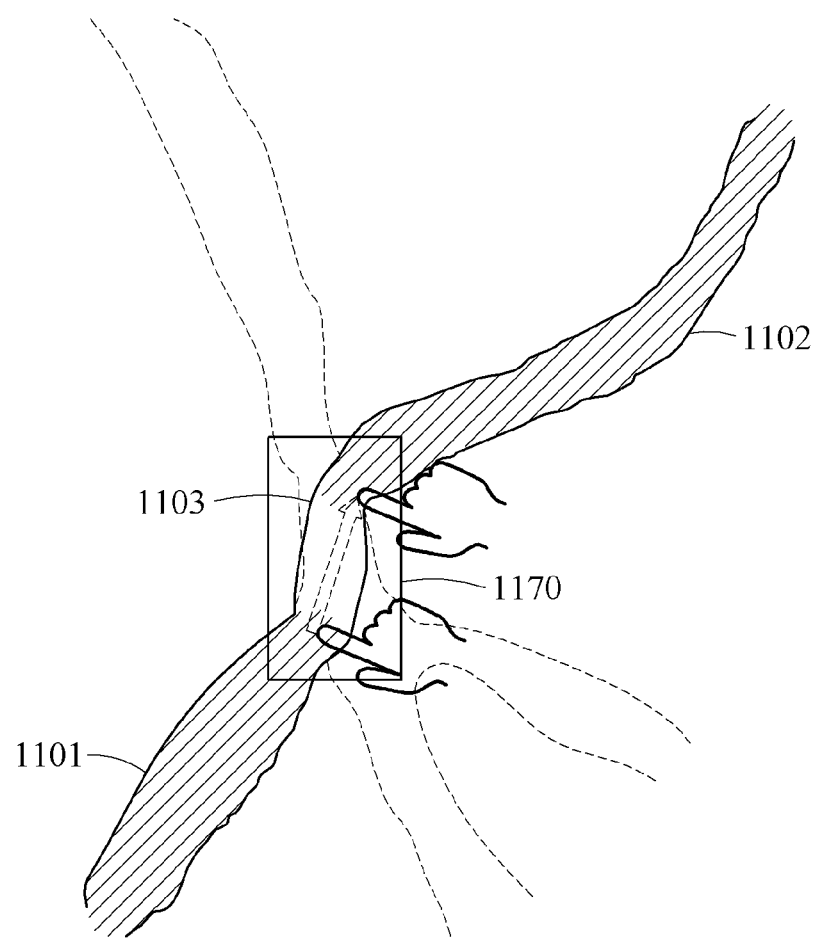

FIGS. 10 and 11 illustrate a method for correcting an error portion according to an example embodiment.

FIG. 10 illustrates correction by the user when the identified error portion is a misidentification portion. According to an example embodiment, the device for processing the blood vessel image may correct the identified error portion on the basis of a user input when the error portion is identified in the target blood vessel. The device for processing the blood vessel image may provide one or more candidate branches to the user in response to a case where the error portion identified in the target blood vessel is the misidentification portion. In response to a case of receiving a selection input for one blood vessel branch among one or more candidate branches from the user, the device for processing the blood vessel image may replace a branch corresponding to the error portion with the selected branch. Illustratively, when the device for processing the blood vessel image first extracts blood vessel branches 1001 and 1002 as a target blood vessel, the device for processing the blood vessel image may determine at least one branch of the blood vessel branches 1001 and 1002 as an error portion in the extraction result for the target blood vessel on the basis of at least one of blood vessel structure data related to the target blood vessel, curvature information of the target blood vessel, diameter information of the target blood vessel, and brightness information of the target blood vessel. The device for processing the blood vessel image may provide the user with one or more candidate blood vessel branches 1010, 1020, and 1030 which are not extracted as the target blood vessel, when the identified error portion is the misidentification portion. An input/output interface of the device for processing the blood vessel image may output graphic objects 1071, 1072, and 1073 that can provide the user with a selection of the candidate blood vessel branches 1010, 1020, and 1030 through a display. The graphic objects may have a shape surrounding regions corresponding to the candidate blood vessel branches. In FIG. 10, the graphic objects 1071, 1072, and 1073 are illustrated in a rectangular shape, but the shape is not limited thereto. The user may select a candidate blood vessel branch by simply clicking or touching a point corresponding to one of the graphic objects corresponding to the candidate blood vessel branches output on the display. That is, when the device for processing the blood vessel image detects a user input with respect to a point corresponding to the graphic object, the device for processing the blood vessel image may determine that a candidate blood vessel branch corresponding to the graphic object is selected, and may replace the blood vessel branch corresponding to the error portion with the selected candidate blood vessel branch. Illustratively, when the device for processing the blood vessel image detects the user input for a point corresponding to the graphic object 1071 from the user, the device for processing the blood vessel image may extract the candidate blood vessel branch 1002 corresponding to the graphic object 1071 as the target blood vessel.

That is, the device for processing the blood vessel image may replace the blood vessel branch 1002 with a blood vessel branch 1010 in the extraction result of the target blood vessel.

FIG. 11 illustrates correction by the user when the identified error portion is a discontinuity portion. According to an example embodiment, the device for processing the blood vessel image may correct the identified error portion on the basis of the user input when the error portion is identified in the target blood vessel. The device for processing the blood vessel image may provide the user with a blood vessel area including the discontinuity portion in response to a case where the error portion identified in the target blood vessel is the discontinuity portion. The device for processing the blood vessel image may connect a region corresponding to a blood vessel branch corresponding to a start point of the user input and a region corresponding to a blood vessel branch corresponding to an end point of the user input, in response to a case where the user input is detected in a plurality of points with respect to the correction result.

In response to a drag input received from the user, the device for processing the blood vessel image according to an example embodiment may connect branches corresponding to the discontinuity portion selected by the drag input. Illustratively, when the device for processing the blood vessel image first extracts blood vessel branches 1101 and 1102 as a target blood vessel, the device for processing the blood vessel image may determine regions corresponding to the blood vessel branches 1101 and 1102 of the extracted target blood vessel as discontinuity portions separated from each other. The input/output interface of the device for processing the blood vessel image may output a graphic object 1170 related to the connection between the regions corresponding to the blood vessel branches 1101 and 1102 through the display. The graphic object 1170 has a shape enclosing the region corresponding to at least a portion of the blood vessel branches 1101 and 1102 corresponding to the discontinuity portions and may represent that the blood vessel branches 1101 and 1102 are connectable by the user. The device for processing the blood vessel image may connect the regions corresponding to the blood vessel branches 1101 and 1102 selected by the drag input and extract a blood vessel branch 1103 between the discontinued blood vessel branches 1101 and 1102 as the target blood vessel, in response to the drag input received from the user. The branches selected by the drag input may indicate a blood vessel branch corresponding to a drag start point and a blood vessel branch corresponding to a drag end point. That is, the device for processing the blood vessel image may include the blood vessel branch 1103 in the extraction result of the target blood vessel.

The device for processing the blood vessel image according to another example embodiment may connect regions between blood vessel branches corresponding to a start point and an end point of a pointing input, in response to the pointing input corresponding to two or more points received from the user. The pointing input is an input indicating one point on the display, and may include, for example, a click input by mouse operation and/or an input by touch operation on a touch display (e.g., touch input). However, the pointing input is not limited thereto, and may include a position indication input by various pointing devices (e.g., a trackball mouse, a touchpad, a trackpad, etc.) according to a design. That is, the device for processing the blood vessel image may receive a click or touch input for the start point and the end point from the user. In response to the pointing input received from the user, the device for processing the blood vessel image may connect a region corresponding to the blood vessel branch corresponding to the start point of the pointing input and a region corresponding to the blood vessel branch corresponding to the end point of the pointing input.

Figure 12:
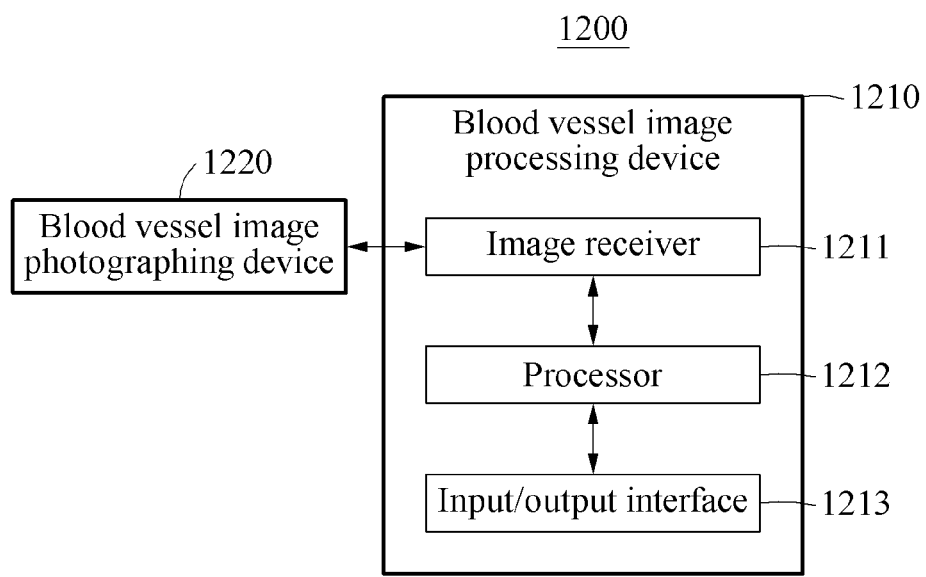
FIG. 12 is a block diagram schematically illustrating a device for processing a blood vessel image according to an example embodiment.

FIG. 12 is a block diagram schematically illustrating a device for processing a blood vessel image according to an example embodiment.

A system 1200 for processing a blood vessel image according to an example embodiment may include a blood vessel image processing device 1210 and a blood vessel image photographing device 1220. The blood vessel image processing device 1210 may include an image receiver 1211, a processor 1212, and an input/output interface 1213. The image receiver 1211 may receive a blood vessel image photographed by the blood vessel image photographing device 1220. The processor 1212 may extract a target blood vessel from the blood vessel image received from the image receiver using a machine learning model, identify an error portion, and correct the identified error portion. The operation of the processor 1212 is not limited thereto, and the processor 1212 may perform the operations described above with reference to FIGS. 1 to 11.

The input/output interface 1213 may receive the input from the user to transmit the received input to the processor. For example, the input/output interface 1213 may receive the input according to a mouse operation, a touch operation, and the like. In addition, the input/output interface 1213 may provide visual feedback to the user. For example, the input/output interface 1213 may output the extraction result of the target blood vessel through the display step by step.

The example embodiments described above may be implemented in hardware components, software components, and/or combinations of hardware components and software components. For example, the device, the method, and the components described in the example embodiments may be implemented using, for example, one or more general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or other any devices capable of executing and responding instructions. The processing device may perform an operating system OS and one or more software applications performed on the operating system. In addition, the processing device may also access, store, manipulate, process, and generate data in response to execution of software. For convenience of understanding, one processing device may be described to be used, but it can be seen to those skilled in the art that the processing device may include a plurality of processing elements and/or a plurality types of processing elements. For example, the processing device may include a plurality of processors or one processor and one controller. In addition, other processing configurations, such as a parallel processor (parallel processor) are also possible.

Software may include computer programs, codes, instructions, or one or more combinations thereof, and may configure the processing device to operate as desired, or to instruct independently or collectively the processing device. Software and/or data are interpreted by the processing device or may be permanently or temporarily embodied in any type of machines, components, physical devices, virtual equipment, computer storage media or devices, or signal waves to be transmitted, in order to provide commands or data to the processing device. The software may be distributed on a computer system connected via a network, and may be stored or executed in a distributed method. The software and data may be stored in one or more computer readable recording media.

The method according to the example embodiment may be implemented in a form of program instructions which may be performed through various computer means to be recorded in computer readable media. The computer readable medium may include program instructions, data files, data structures, and the like alone or in combination. The program instructions recorded in the medium may be specially designed and configured for the example embodiments or may be publicly known to and used by those skilled in the computer software art. Examples of the computer readable record media include magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program instructions. Examples of the program instructions include high language codes executable by a computer using an interpreter and the like, as well as machine language codes created by a compiler. The hardware devices may be configured to operate as one or more software modules in order to perform the operations of the embodiments, and vice versa.

As described above, although the example embodiments have been described by the restricted drawings, various modifications and variations can be applied based on the example embodiments by those skilled in the art. For example, even if the described techniques are performed in a different order from the described method, and/or components such as a system, a structure, a device, a circuit, and the like described above are coupled or combined in a different form from the described method, or replaced or substituted by other components or equivalents, an appropriate result can be achieved.

The invention claimed is:

1. A method for processing a blood vessel image performed by a processor comprising the steps of:
   extracting a target blood vessel from a blood vessel image;
   identifying an error portion of the blood vessel image from the extraction result of the target blood vessel on the basis of brightness information of the target blood vessel, wherein the brightness information of the target blood vessel includes an indication of a concentration of a contrast agent that has been injected into a bloodstream flowing within the target blood vessel; and
   correcting the identified error portion of the blood vessel image in response to a case where the error portion of the blood vessel image is identified from the extraction result of the target blood vessel,
   wherein the identifying the error portion of the blood vessel image comprises identifying a lower branch as a misidentification portion of the blood vessel image in response to a case where a brightness difference between an upper branch and the lower branch adjacent to each other is a threshold brightness difference or more in the extraction result of the target blood vessel,
   wherein the correcting the identified error portion of the blood vessel image comprises replacing the lower branch with another candidate lower branch having a brightness difference from the upper branch of less than the threshold brightness difference, and
   wherein the threshold brightness difference is determined based on a type of the target blood vessel.

2. The method for processing the blood vessel image of claim 1, wherein the identifying of the error portion of the blood vessel image is also on the basis of blood vessel structure data related to the target blood vessel and further comprises
   segmenting a blood vessel area and a non-blood vessel area from the blood vessel image;
   generating the blood vessel structure data on the basis of a node corresponding to each of blood vessel branches divided based on a branch point in the blood vessel area;
   comparing connection data between nodes of the target blood vessel with the blood vessel structure data; and
   determining nodes corresponding to a connection error as the error portion of the blood vessel image when the connection error between the nodes is detected on the basis of a topology of the blood vessel structure data.

3. The method for processing the blood vessel image of claim 2, wherein the correcting of the identified error portion of the blood vessel image comprises
   connecting regions corresponding to a discontinuity portion in response to a case where the error portion of the blood vessel image is identified as the discontinuity portion; and
   replacing a node corresponding to a misidentification portion with a node matching the blood vessel structure data in response to a case where the error portion of the blood vessel image is identified as the misidentification portion.

4. The method for processing the blood vessel image of claim 1, wherein:
   the identifying of the error portion of the blood vessel image is also on the basis of blood vessel structure data related to the target blood vessel and further comprises
      identifying a lower branch as a misidentification portion in response to a case where a curvature between an upper branch and the lower branch adjacent to each other exceeds a threshold curvature in the extraction result of the target blood vessel; and
   the correcting of the identified error portion of the blood vessel image comprises
      replacing the lower branch with another candidate lower branch having a curvature with the upper branch of the threshold curvature or less with respect to the identified misidentification portion.

5. The method for processing the blood vessel image of claim 1, wherein
   the correcting of the identified error portion of the blood vessel image comprises
   generating a new extraction result for the target blood vessel in response to a case where the error portion of the blood vessel image is identified.

6. The method for processing the blood vessel image of claim 1, wherein
   the correcting of the identified error portion of the blood vessel image comprises
   providing a user with one or more candidate branches in response to a case where the error portion of the blood vessel image is the misidentification portion; and
   replacing a branch corresponding to the error portion of the blood vessel image with the selected branch in response to a case of receiving a selection input for one branch among the one or more candidate branches from the user.

7. The method for processing the blood vessel image of claim 1, wherein the correcting of the identified error portion of the blood vessel image comprises connecting a region corresponding to a blood vessel branch corresponding to a start point of a user input and a region corresponding to a blood vessel branch corresponding to an end point of the user input, in response to a case where the user input is detected in a plurality of points.

8. A method for processing a blood vessel image performed by a processor comprising the steps of:

extracting a target blood vessel from a blood vessel image;

identifying an error portion of the blood vessel image from the extraction result of the target blood vessel on the basis of diameter information of the target blood vessel, and brightness information of the target blood vessel, wherein the diameter information includes identifying a diameter difference between an upper branch and a lower branch adjacent to each other in the blood vessel image is a threshold or more in the extraction result of the target blood vessel and the brightness information of the target blood vessel includes an indication of a concentration of a contrast agent that has been injected into a bloodstream flowing within the target blood vessel; and correcting the identified error portion of the blood vessel image in response to a case where the error portion of the blood vessel image is identified from the extraction result of the target blood vessel, wherein the identifying the error portion of the blood vessel image comprises identifying a lower branch as a misidentification portion of the blood vessel image in response to a case where a brightness difference between an upper branch and the lower branch adjacent to each other is a threshold brightness difference or more in the extraction result of the target blood vessel wherein the correcting the identified error portion of the blood vessel image comprises replacing the lower branch with another candidate lower branch having a brightness difference from the upper branch of less than the threshold brightness difference, and wherein the threshold brightness difference is determined based on a type of the target blood vessel.

9. The method for processing the blood vessel image of claim 8, wherein the correcting of the identified error portion of the blood vessel image comprises correcting the identified error portion of the blood vessel image by performing at least one of replacing the lower branch on the basis of the diameter difference from the upper branch with respect to the identified error portion of the blood vessel image and generating a new extraction result including new diameter information about the target blood vessel.

10. A device for processing a blood vessel image comprising:

an image receiver for receiving a blood vessel image; and a processor for extracting a target blood vessel from the blood vessel image, identifying an error portion of the blood vessel image from the extraction result of the target blood vessel on the basis of brightness information of the target blood vessel, wherein the brightness information of the target blood vessel includes an indication of a concentration of a contrast agent that has been injected into a bloodstream flowing within the target blood vessel, and correcting the identified error portion of the blood vessel image in response to a case where the error portion of the blood vessel image is identified from the extraction result of the target blood vessel, wherein the processor identifies a lower branch as a misidentification portion of the blood vessel image in response to a case where a brightness difference between an upper branch and the lower branch adjacent to each other is a threshold brightness difference or more in the extraction result of the target blood vessel, and replaces the lower branch with another candidate lower branch having a brightness difference from the upper branch of less than the threshold brightness difference, wherein the threshold brightness difference is determined based on a type of the target blood vessel.

* * * * *